United States Patent
Chorev et al.

(10) Patent No.: US 6,251,938 B1
(45) Date of Patent: *Jun. 26, 2001

(54) PHENYLETHYLAMINE DERIVATIVES

(75) Inventors: Michael Chorev, Jerusalem; Tamar Goren, Rehovot; Yacov Herzig, Ra'ananna; Jeffrey Sterling; Marta Weinstock-Rosin, both of Jerusalem; Moussa B. H. Youdim, Haifa, all of (IL)

(73) Assignees: Teva Pharmaceutical Industries, Ltd.,, Petach-Tikva; Technion Research and Development Foundation, Ltd.,, Haifa; Yissum Research Development Company of the Hebrew University of Jerusalem, Jerusalem, all of (IL)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 60 days.

(21) Appl. No.: 09/335,555

(22) Filed: Jun. 18, 1999

Related U.S. Application Data

(63) Continuation of application No. PCT/US97/23897, filed on Dec. 18, 1997.

(30) Foreign Application Priority Data

Dec. 18, 1996 (IL) .......................................... 119852
Mar. 24, 1997 (IL) .......................................... 120509

(51) Int. Cl.[7] .................. A61K 31/27; C07C 333/00; C07C 271/00
(52) U.S. Cl. .................. 514/484; 514/490; 558/234; 560/115; 560/136
(58) Field of Search .................. 558/234; 560/115, 560/136; 514/484, 490

(56) References Cited

U.S. PATENT DOCUMENTS

| 3,507,962 | 4/1970 | Taylor . |
| 3,513,240 | 5/1970 | Bernardus et al. . |
| 4,948,807 | 8/1990 | Rosin et al. . |
| 5,273,974 | 12/1993 | Goto et al. . |
| 5,602,176 | 2/1997 | Enz . |

FOREIGN PATENT DOCUMENTS

| 664291A1 | 10/1993 | (EP) . |
| 614888A1 | 2/1994 | (EP) . |
| WO9100724 | 1/1991 | (WO) . |
| WO9602524 | 2/1996 | (WO) . |

OTHER PUBLICATIONS

Martin et al., "Discriminant Analysis of the Relationship Between Physical Properties and the Inhibition of Monoamine Oxidase by Aminotetralins and Aminoindans", *J. Med. Chem.* (1974) 17(4):409–413 (Exhibit 1).

Caplus abstract of JP 54132559, Apr. 1978.*

Chorvat et al. "Acetycholine Release Enhancing Agents: Potential Therapeutics For Alzheimer's Disease"(1995), Drugs of the Future 20(11):1145–1162 (Exhibit 10).

Cooper et al. "Alzheimer's Disease Drug Treatment" (1993), J. Ger. Drug Ther. 8(2):5–18 (Exhibit 11).

Cutler et al. "Muscarinic M1–Receptor Agonists" (1995), CNS Drugs 3(6):467–481 (Exhibit 12).

Davis et al. "Tacrine" (1995), The Lancet 345:625–630 (Exhibit 13).

Drugs of the Future 1991, 16(1), 16–18 (Exhibit 14).

Drugs of the Future 1995, 20(1), 77–78 (Exhibit 15).

Drugs of the Future 1995, 20(3), 248–250 (Exhibit 16).

Fink et al. "Imino 1,2,3,4–Tetrahydrocyclopent[B]indole Carbamates as Dual Inhibitors of Acetylcholinesterase and Monoamine Oxidase" (1996), Bioorganic & Medical Chemistry Letters 6(6), 625–630 (Exhibit 17).

Gabryel et al. Nootropics: Pharmacological Properties and Therapeutic Use (1994), Pol. J. Pharmacol.46:383–394 (Exhibit 18).

Harvey "The Pharmacology of Galantamine and its Analogues" (1995), Pharmac. Ther. 68(1):113–128 (Exhibit 19).

Hori et al. Database CAPLUS on STN®, Chemical Abstracts Service, (Columbus, Ohio), Accession No. 1980:180807, 'N–containing diphenylethylamine derivatives and acid adducts', abstract, Japan Kokai Tokkyo Koho JP 54–132559, Oct. 15, 1979, abstract (Exhibit 20).

Knapp et al. "A 30–Week Randomized Controlled Trial of High–Dose Tacrine in Patients with Alzheimer's Disease" (1994), JAMA 271(13):985–991 (Exhibit 21).

Sramek et al. "Safety/Tolerability Trial of SDZ ENA 713 in Patients with Probable Alzheimer's Disease" (1996), Life Sciences 58(15):1201–1207 (Exhibit 22).

Tariot et al. "Treatment of Alzheimer's Disease: Glimmers of Hope" (1993), Chem. Ind. 20, 801–3, 806–7 (Exhibit 23).

Terni et al. Database CAPLUS on STN®, Chemical Abstracts Service (Columbus, Ohio),, Accession No. 1996:340192 Preparation of (aminoalkyl) phenyl morpholinoalkylcarbamates and analogs as cholinesterase inhibitors, abstract, WO 96/02524, Feb. 1, 1996, see entire abstract (Exhibit 24); and.

Weinstock, "The Pharmacotherapy of Alzheimer's Disease Based on the Cholinergic Hypothesis: an Update" (1995), Neurodegeneration 4:349–356 (Exhibit 25).

* cited by examiner

*Primary Examiner*—Howard C. Lee
*Assistant Examiner*—Leigh C. Maier
(74) *Attorney, Agent, or Firm*—John P. White; Cooper & Dunham LLP

(57) ABSTRACT

This invention is directed to compounds of the following formula:

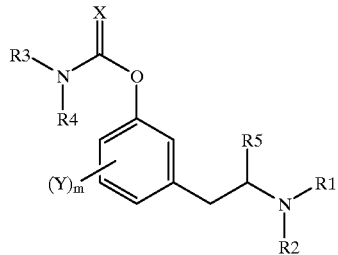

wherein m is from 0–4; X is O or S; Y is halogeno; $R_1$ is hydrogen or $C_{1-4}$ alkyl; $R_2$ is hydrogen, $C_{1-4}$ alkyl or optionally substituted propargyl; and $R_3$ and $R_4$ are each independently hydrogen, $C_{1-8}$ alkyl, $C_{6-12}$ aryl, $C_{6-12}$ cycloalkyl or $C_{6-12}$ aralkyl, $R_5$ is hydrogen or $C_{1-4}$ alkyl; and pharmaceutically acceptable salts thereof, provided that when X is O, $R_2$ is optionally substituted propargyl.

This invention is also directed to the use of these compounds for treating depression, Attention Deficit Disorder (ADD), Attention Deficit and Hyperactivity Disorder (ADHD), Tourette's Syndrome, Alzheimer's Disease and other dementia's such as senile dementia, dementia of the Parkinson's type, vascular dementia and Lewy body dementia.

This invention is further directed to a pharmaceutical composition comprising a therapeutically effective amount of the above-defined compounds and a pharmaceutically acceptable carrier.

28 Claims, 1 Drawing Sheet

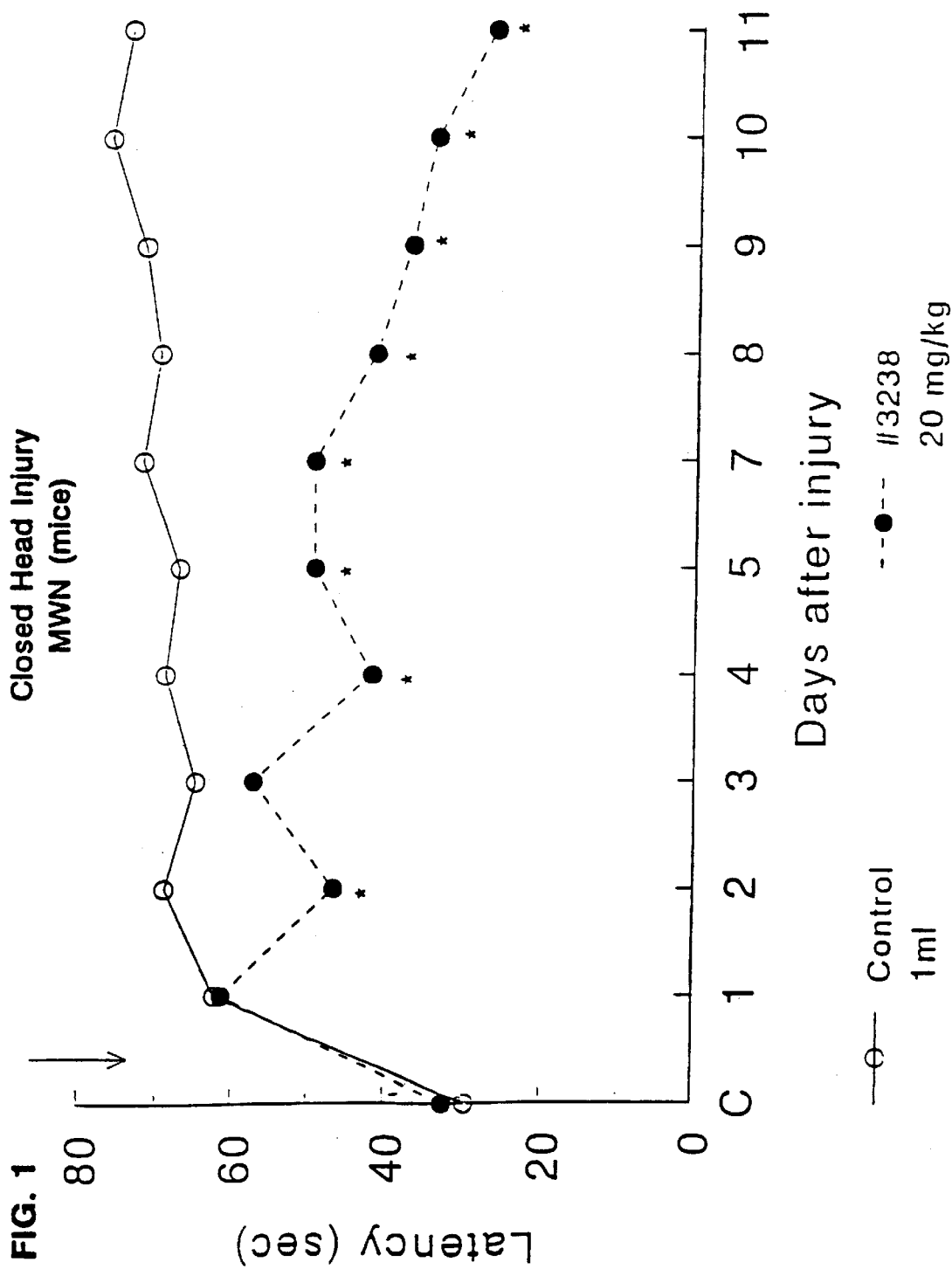

PHENYLETHYLAMINE DERIVATIVES

This application is a continuation of PCT International Application No. PCT/US97/23897, filed Dec. 18, 1997, designating the United States of America, which is claiming priority of Israeli Patent Application Nos. 119852, filed Dec. 18, 1996 and 120509, filed Mar. 24, 1997, the contents of which are hereby incorporated by reference into the present application.

FIELD OF INVENTION

The present invention relates to novel compounds, pharmaceutical compositions containing said compounds and their use in the treatment of various CNS disorders.

BACKGROUND TO THE INVENTION

Dementia may take several forms including static dementia, Alzheimer's-type dementia, senile dementia, pre-senile dementia and progressive dementia. One of the common pathological features of several types of dementia is the lack of the neurotransmitter acetylcholine. This has led to the development of acetylcholine esterase inhibitors for use in the treatment of dementia's such as the compound tacrine.

Recently, compounds that in addition to inhibiting acetylcholine esterase, have inhibitory activity against monoamine oxidase type A (MAO-A) have been developed. The perceived benefit of having the anti-MAO-A activity is stated to be an anti-depressant effect (European Patent Applications Publication Nos. 614,888 and 664,291) Fink et al., (Bioorg & Med Chem Letts (1996) 6 625-630) also disclose compounds having both acetylcholine esterase and monoamine oxidase inhibitory moieties.

International Patent Application Publication No. WO96/02524 relates to alkylamino substituted phenylcarbamate derivatives having acetylcholinesterase inhibitory activity and their use in the treatment of Alzheimer's Disease.

SUMMARY OF THE INVENTION

The present invention compounds of formula I having the following formula:

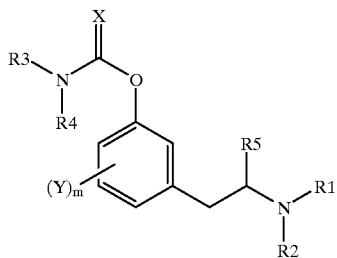

I wherein m is from 0–4; X is O or S; Y is halogeno; R, is hydrogen or $C_{1-4}$ alkyl; $R_2$ is hydrogen, $C_{1-4}$ alkyl or optionally substituted propargyl; $R_3$ and $R_4$ are each independently hydrogen, $C_{1-8}$ alkyl, $C_{6-12}$ aryl, $C_{6-12}$ cycloalkyl or $C_{6-12}$ aralkyl; and $R_5$ is hydrogen or $C_{1-4}$ alkyl, with the proviso that when X is O, $R_2$ is optionally substituted propargyl;

As used hereinafter, references to the compounds of formula I include all compounds of formula I without the final proviso.

The invention relates to the compounds themselves, pharmaceutical compositions containing said compounds and their use in the treatment of depression, Attention Deficit Disorder (ADD), Attention Deficit and Hyperactivity Disorder (ADHD), Tourette's Syndrome, Alzheimer's Disease and other dementia's such as senile dementia, dementia of the Parkinson's type, vascular dementia and Lewy body dementia.

A further aspect of the present invention relates to the use of the compounds of formula I wherein m is from 0–4; X is O or S; Y is halogeno; $R_1$ is hydrogen or $C_{1-4}$ alkyl; $R_2$ is hydrogen, $C_{1-4}$ alkyl or optionally substituted propargyl; $R_3$ and $R_4$ are each independently hydrogen, $C_{1-8}$ alkyl, $C_{6-12}$ aryl, $C_{6-12}$ cycloalkyl or $C_{6-12}$ aralkyl; and R is hydrogen or $C_{1-4}$ alkyl, in the treatment of neurotrauma, memory disorder or depression.

As used herein the term "neurotrauma" includes, but is not limited to, damage caused to the nervous system (both central and peripheral) by virtue of ischemic damage such as stroke, hypoxia or anoxia, neurodegenerative diseases, Parkinson's Disease, Alzheimer's Disease, Huntington's Disease, neurotoxic injury, head trauma injury, spinal trauma injury, peripheral neuropathy and any form of nerve damage.

The present invention relates to the racemic compounds themselves and optically active isomers thereof.

DESCRIPTION OF THE PREFERRED EMBODIMENTS

The present invention is directed to compounds having the following formula:

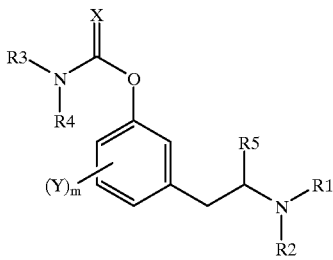

wherein
m is from 0–4;
X is O or S;
Y is halogeno;
$R_1$ is hydrogen or $C_{1-4}$ alkyl;
$R_2$ is hydrogen, $C_{1-4}$ alkyl or optionally substituted propargyl; and $R_3$ and $R_4$ are each independently hydrogen, $C_{1-8}$ alkyl, $C_{6-12}$ aryl, $C_{6-12}$ cycloalkyl or $C_{6-12}$ aralkyl, $R_5$ is hydrogen or $C_{1-4}$ alkyl; and pharmaceutically acceptable salts thereof, provided that when X is O, $R_2$ is optionally substituted propargyl.

In an embodiment of the present invention, X is O. In a further embodiment of the present invention, X is S.

In an embodiment of the present invention, the compound is selected from the group consisting of: (rac)-3-(N-methyl, N-propyl-carbamyloxy)-α-methyl-N'-propargyl phenethylamine HCl; (rac)-3-(N,N-dimetlhyl-carbamyloxy)-α-methyl-N'-methyl,N'-propargyl phenethylamine HCl; (rac)-3-(N-methyl,N-hexyl-carbamyloxy)-α-methyl-N'-methyl, N'-propargyl phenethylamine mesylate; (rac)-3-(N-methyl, N-cyclohexyl-carbamyloxy)-α-methyl-N'-methyl,N'-methyl,N'-propargyl phenethylamine HCl; and (S)-3-(N-methyl, N-hexyl-carbamyloxy)-α-methyl-N'-methyl,N'-propargyl phenethylamine ethanesulfonate.

A first object of the present invention relates to the compounds of formula I and their use in the treatment of Alzheimer's Disease and related dementias.

In an embodiment of the present invention $R_1$ is hydrogen., methyl or ethyl. When $R_2$ is propargyl then it may optionally be substituted. Such substitution is preferably on the methylene group (see $R_6$ in Scheme I) and is selected from the group consisting of $C_{1-4}$ alkyl.

According to the present invention, "halogeno" is used to refer to fluoro, chloro, bromo or iodo.

In an embodiment of the present invention, when m is greater than 1, each Y may be the same or different.

In a further embodiment of the present invention, at least one of $R_3$ and $R_4$ is methyl and the other is hydrogen, methyl, ethyl propyl, hexyl or cyclohexyl. In an additional embodiment of the present invention, $R_5$ is hydrogen or methyl.

The subject invention further provides pharmaceutically acceptable salts of the compounds of formula I. Examples of pharmaceutically acceptable salts include, but are not limited to, esylate salts, mesylate salts, maleate salts, fumarate salts, tartrate salts, hydrochloride salts, hydrobromide salts, p-toluenesulfonate salts, benzoate salts, acetate salts, phosphate salts and sulfate salts.

The subject invention further provides a pharmaceutical composition which comprises a therapeutically effective amount of a compound of formula I or a pharmaceutically acceptable salt thereof and a pharmaceutically acceptable carrier. The "therapeutically effective amount" of a compound of formula I or a pharmaceutically acceptable salt thereof may be determined according to methods well known to those skilled in the art.

The compositions of the present invention may be prepared as medicaments to be administered orally, parenterally, rectally, or transdermally.

Suitable forms for oral administration include tablets, compressed or coated pills, dragees, sachets, hard or soft gelatin capsules, sublingual tablets, syrups and suspensions. In one embodiment, the pharmaceutically acceptable carrier is a solid and the pharmaceutical composition is a tablet.

The therapeutically effective amount may be an amount from about 0.5 mg to about 2000 mg, preferably, from about 1 mg to about 100 mg.

In an alternative embodiment, the pharmaceutically acceptable carrier is a liquid and the pharmaceutical composition is an injectable solution. The therapeutically effective amount may be an amount from about 0.5 mg to about 2000 mg, preferably from 1 mg to about 1000 mg. The volume administered may bean amount between 0.5 and 10 ml.

In a further alternative embodiment, the carrier is a gel and the pharmaceutical composition is a suppository. For parenteral administration the invention provides ampoules or vials that include an aqueous or non-aqueous solution or emulsion. For rectal administration there are provided suppositories with hydrophilic or hydrophobic vehicles. For topical application as ointments and transdermal delivery there are provided suitable delivery systems as known in the. art. For oral or suppository formulations, 0.5–2000 mg per unit dosage, and preferably 1–1000 mg per dosage unit is taken daily.

These compositions may be used alone to treat the above-listed disorders, or alternatively, as in the case of Alzheimer's Disease, for example, they may be used as an adjunct to the conventional treatments such as haloperidol, tacrine or deprenyl.

The invention will be better understood from the Experimental Details which follow. However, one skilled in the art will readily appreciate that the specific methods and results discussed are merely illustrative of the invention as described more fully in the claims which follow thereafter.

Experimental Details

Introduction

Compounds of general formula I may be prepared (as shown in Scheme I) from the corresponding carbamoyl derivatives of phenethylamine IV by reacting the latter with propargyl compounds bearing an appropriate leaving group at the 3-position, e.g. a halide group, mesylate, tosylate, etc., under basic conditions provided by an inorganic base, e.g. $K_2CO_3$, NaOH, or an organic base e.g. a tertiary amine, in a polar organic solvent, e.g. $CH_3CN$, DMF, etc., at 15–40° C., preferably at 20–25° C., for a period of time in the range of 5–24 hours, preferably 5–10 hours. The products, obtained after a suitable work-up and purification, are in the form of free bases. Preferably these are converted into their pharmaceutically acceptable salts.

Compounds of general formula IV may be prepared by Boc deprotection of compounds of general formula III. Preferably the deprotected compounds obtained are converted into their hydrochloride salts. Compounds of general formula III may be prepared by carbamylating a compound of general formula II in a conventional manner, e.g. by reacting the compound of formula II with an appropriate carbamoyl halogenide or an alkylisocyanate.

Compounds of general formula II may be prepared by Boc protection of the appropriate hydroxy phenethylamines, by methods known to those skilled in the art.

Compounds of general formula I, where $R_1$ is not H, may also be prepared (as shown in scheme II) by carbamylation of VII, by the same method described above for the carbamylation of II. Compounds of general formula VII may be prepared by propargylation of the 3-hydroxy phenethylamines of general formula VI, by methods analogous to those described for the propargylation of IVVI.

N,N dialkyl substituted compounds of formula I may be prepared by the carbamylation of compounds of formula V or he N-alkylation of compounds of formula IV.

Starting Materials

3-Hydroxy-phenethylamine and its N-methyl analogue were obtained by demethylation of 3-methoxy phenethylamine and N-methyl-3-methoxy phenethylamine. The latter was prepared from 3-methoxy phenethylamine by reductive alkylation (ethyl formate, followed by lithium aluminium hydride).

N,N-Dimethyl-3-hydroxy phenethylamine was prepared by reductive amination (H2,Pd/C,$Me_2NH$) of (3-methoxyphenyl) acetonitrile:, followed by O-demethylation.

3-Hydroxy-methyl phenethylamine was obtained by O-demethylation of the corresponding 3-methoxy analogue. The latter may be prepared by reductive amination ($NaCNEH_3$,$NH_4OAc$)[2] of 3-methoxyphenyl acetone[3] or by reduction of 1-(3-methoxyphenyl)-2-nitro-1-propene (obtained by condensing 3-methoxy benzaldehyde with nitroethane)[4]. 3-Hydroxy-,N-dimethyl phenethylamine was prepared by O-demethylation of the corresponding 3-methoxy analogue. The latter was obtained by the reductive amination (methylamine, $NaCNBH_3$)[2] of 3-methoxyphenyl acetone[3].

Alternatively, 3-hydroxy-(α,N-dimethyl phenethylamine may be prepared by reductive methylation (N-formylation followed by reduction) of 3-hydroxy-α-methyl phenethylamine.

REFERENCES:

1. J S Buck et al., *J. Amer. Chem. Soc.* (1938) 60: 1789
2. R F Borch et al., *J. Amer. Chem. Soc.* (1971) 93: 2897
3. Org. Synth. Coll. Vol IV, (1963) 573; and
4. A Carlsson, et al., *Acta. Pharm. Suecica.* (1970) 7: 293.

Preparation of Compounds of the Present Invention

A. Boc—protection and carbamylation

1. Boc protection (3-hydroxy-N-Boc,N-methyl phenethylamine)

To a solution of 3-hydroxy N-methyl phenethylamine (8.33 g, 55.17 mmol) in dioxane (80 ml) and water (80 ml)

was added NaHCO₃ (13.65 g) and di-t-butyl dicarbonate (13.65 g, 62.54 mmol). The reaction mixture was stirred at room temperature (RT) for 4 hrs and evaporated to dryness in-vacuo. The residue was taken up in a water:dioxane mixture (400 ml, 1:1), and the layers were separated. The aqueous layer was re-extracted with ether (2×75 ml) and the combined ether layer was dried (Na₂SO₄) and evaporated to dryness in-vacuo. The oily residue was purified by column chromatography (hexane:EtOAc 2:1) to give 10.2 g (74%) of the title compound as a viscous yellow oil.

2. Carbamylation 3-(N-Me,N-nPr carbamyloxy) N-Boc,N-methyl phenethylamine

To an ice-cooled solution of 3-hydroxy-N-Boc,N-methyl phenethylamine (5.0 g, 19.9 mmol) in dry acetonitrile (65 ml) was added under nitrogen, N-methyl,N-n-propyl carbamoyl chloride (4.66 g, 34.43 mmol), followed by the portionwise addition of NaH (60% disp. in oil, 1.03 g, 25.87 mmol). The reaction mixture was stirred at RT under nitrogen for 6 hrs and evaporated to dryness in-vacuo. Water (200 ml) was added, the pH was adjusted to ~9 and the aqueous layer was extracted with ether (4×100 ml). The combined ether layer was washed with NaOH solution (pH 9.5), water (150 ml), dried (Na₂SO₄) and evaporated to dryness in-vacuo to give an oil which was purified by column chromatography (hexane:EtOAc 2:1), affording 6.0 g (86%) of the title compound as a yellow oil.

According to these methods the exemplary intermediates in Table 1 were prepared.

TABLE 1

N-Boc Protected carbamyloxy-phenylethylamines

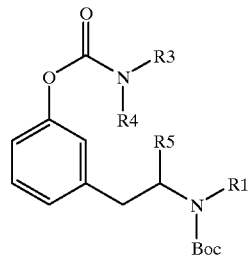

| R1 | R3 | R4 | R5 | yield (%) |
|----|----|----|----|-----------|
| H  | Me | Me | H  | 85 |
| H  | Me | Pr | H  | 89 |
| Me | Me | Me | H  | 86 |
| H  | Me | Et | H  | 83 |
| Me | Me | Et | H  | 78 |
| Me | Me | Pr | H  | 86 |
| H  | Me | Me | Me | 80 |
| H  | Me | Et | Me | 92 |
| H  | Me | Pr | Me | 98 |

B. Boc—Deprotection and Salt Formation 3-(N-Me,N-nPr Carbamyloxy) N-methyl phenethylamine HCl (Compound 6)

3-(N-Me,N-nPr Carbamyloxy) N-Boc,N-methyl phenethylamine (6.0 g, 17.14 mmol) was dissolved in dioxane (60 ml) and 20% HCl/ether (60 ml) was added. The mixture was stirred at RT for 4 hrs and evaporated to dryness in-vacuo, and the residual oil was treated with ether (2×150 ml), to give, after stirring and ice-cooling, 4.6 g (93.5%) of the title compound as a white solid. In this manner the compounds shown in Table 2 were prepared, their analytical characteristics are given in Table 4.

TABLE 2

Carbamyloxy-phenylethylamines (HCl salts)

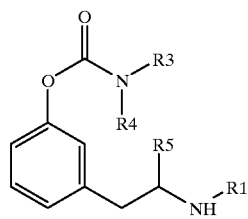

| Compound # | R1 | R3 | R4 | R5 | cryst/slurry solvent | mp (° C.) | yield (%) |
|---|----|----|----|----|----|----|----|
| 1  | H     | Me | Me       | H  | Et₂O       | 125–7       | 86 |
| 2  | H     | Me | Pr       | H  | Et₂O       | 83–5        | 85 |
| 3  | Me    | Me | Me       | H  | Et₂O       | 126–8       | 94 |
| 4  | H     | Me | Et       | H  | Et₂O       | 103–5       | 95 |
| 5  | Me    | Me | Et       | H  | Et₂O       | —           | 68 |
| 6  | Me    | Me | Pr       | H  | Et₂O       | 86–8        | 93 |
| 7  | H     | Me | Me       | Me | Et₂O       | —           | 80 |
| 8  | H     | Me | Et       | Me | Et₂O       | —           | 81 |
| 9  | H     | Me | Pr       | Me | Et₂O       | —           | 78 |
| 10 | Me, Me | Me | Me      | H  | iPrOH.Et₂O | 127–9       | 49 |
| 23 | H     | H  | Pr       | H  | Et₂O       | 205–7       |    |
| 24 | Me    | Me | n-hexyl  | Me | Et₂O       | hygroscopic | 89 |
| 25 | Me    | Me | cyclohexyl | Me | Et₂O     | —           | 95 |

C. Propargylation and Salt Formation
(N-Me,N-Et Carbamyloxy)α-methyl, N-proparayl nethylamine.HCl (Compound 17)

A solution of propargyl bromide (1.1 g, 9.1 mmol) in acetonitrile (8.5 ml) was added dropwise to a stirred mixture of 3-(N-Me, N-Et carbamyloxy)α-methyl phenethylamine-.HCl (2.4 g, 8.8 mmol) and potassium carbonate (2.8 g) in acetonitrile (25 ml), and the mixture was stirred at RT for 7 hrs. The reaction mixture was filtered and the filtrate was removed under reduced pressure and the residue was purified by column chromatography (hexane:EtOAc 2:1) to give 1.76 g of the title compound as the free base (73%)

The free base was dissolved in dry ether (50 ml) and HCl/ether was added (to pH 1). The mixture was stirred for 4 hrs at RT, filtered and the solid was washed with cold ether, to give, after drying at 60° C. in-vacuo, 1.5 g (4.82 mmol, 55%).

3-(N-Me,N-nPr carbamyloxy)N-methyl,N-propargyl phenethylamine.HCl (Compound 18)

To a stirred mixture of 3-(N-Me,N-nPr carbamyloxy)N-methyl phenethylamine.HCl (4.02 g, 14.0 mmol) and potassium carbonate (3.87 g, 28.0 mmol) in acetonitrile (150 ml), was added dropwise at RT a solution of propargyl bromide (1.67 g, 14.0 mmol) in acetonitrile (10 ml). The reaction mixture was stirred at RT for 21 hrs, filtered and the filtrate evaporated to dryness in-vacuo and the residual orange oil (4.1 g) was purified by column chromatography (EtOAc) to give 2.7 g of the free base The free base (1.35 g, 4.69 mmol) was dissolved in dry ether (70 ml) and HCl/ether (7 ml) was added dropwise. The mixture was stirred at RT for ½ hr and the supernatant was decanted off. The gummy residue was crystallized twice from iPrOH/ether to give 1.16 g (51.4%) of a white solid.

The methods were repeated and the following compounds of the present invention were prepared (Table 3), their analytical characteristics are given in Table 5.

D. Proparaylation of 3-hydroxy phenethylamines
(S)-3-Hydroxvy-α,N-dimethvl-N-proparayl-phenethylamine (Compound 42)

To a solution of (S)-³-Hydroxy-α,N-dimethyl phenethylamine.HCl (4.4 g, 21.8 mmol) in dimethylacetamide (200 ml) stirred at 25° C. under a nitrogen atmosphere, was added K$_2$CO$_3$ (6.04 g, 43.64 mmol), and the mixture was stirred for 10 minutes. Then a solution of propargyl bromide (2.34 g, 19.64 mmol) in dimethylacetamide (10 ml) was added over 2 minutes and the mixture was stirred at 25° C. for 24 hours.

Water (250 ml) was added and the mixture was stirred until all the solid material dissolved. The aqueous layer was extracted with toluene (10×75 ml). The layers were separated and the combined toluene layer was washed with saturated brine (2×150 ml) and dried (Na$_2$SO$_4$) Removal of solvent at reduced pressure gave an orange oil, which was purified by flash column chromatography using ethyl acetate as the eluent. This gave 3.60 g (90.2t) of Compound 42 as an orange oil.

Using this procedure, the (R) isomer (Compound 41) was obtained in 80%.

E. Carbamylation and salt formation
(S) 3- (N-methyl,N-ethyl-carbamyloxy)-(α,N-dimethyl-N-propar gyl-phenethylamine esylate (Compound 39)

To a solution of compound 42 (1.80 g, 8.87 mmol) in dry acetonitrile (100 ml) cooled in an ice bath, was added under nitrogen N-methyl-N-cyclohexylcarbamyl chloride (2.70 g, 15.39 mmol) followed by the portionwise addition of NaH (60% oil dispersion, 0.467 g, 11.69 mmol). The mixture was then stirred at RT under nitrogen for 18 hours. Solvent was removed at reduced pressure and water (100 ml) and ether (150 ml) were added. The mixture was stirred until all the material dissolved. The layers were separated and the aqueous layer was reextracted with ether (4×70 ml). The combined ether layers were washed with KOH solution (pH 9.5), water and dried (Na$_2$SO$_4$).

Removal of solvent at reduced pressure gave 3.87 g of an orange oil which was purified by flash column chromatography using the ethyl acetate as the eluent. This gave 2.57 g (84.5%) of the title compound (free base) as a yellow oil.

The free base was dissolved in dry EtOAc (9 ml) and a solution of 95% ethanesulfonic acid (0.79 g, 6.81 mmol) in EtOAc (1.5 ml) was added. The solution was cooled to 5° C. and stirred at this temperature. After about 15 minutes, a white solid precipitated and it was stirred at 5° C. for 3 hours. The solid was filtered using a minimum amount of ice-cold ethyl acetate. This gave 2.3 g (75%) of a white solid having a melting point of 118–120° C.

The methods were repeated and the following compounds of the present invention were prepared (Table 3a), their analytical characteristics are given in Table 5.

TABLE 3

Carbamyloxy-N-propargyl-phenylethylamines (HCl salts)

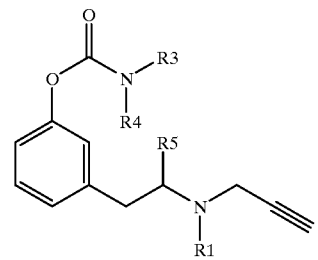

| Compound # | R1 | R3 | R4 | R5 | cryst/slurry solvent | mp (° C.) | yield (%) |
|---|---|---|---|---|---|---|---|
| 11 | H | Me | Me | H | iPrOH/Et$_2$O | 138–9 | 47 |
| 12 | Me | Me | Me | H | iPrOH/Et$_2$O | 150–2 | 54 |
| 13 | H | Me | Et | H | iPrOH/Et$_2$O | 113–15 | 36 |
| 14 | H | me | Pr | H | iPrOH/Et$_2$O | 108–10 | 20 |
| 15 | Me | Me | Et | H | iPrOH/Et$_2$O | 152–4 | 41 |
| 16 | H | Me | Me | Me | Et$_2$O | 166–70 | 34 |
| 17 | H | Me | Et | Me | Et$_2$O | 119–121 | 60 |
| 18 | Me | Me | Pr | H | iPrOH/Et$_2$O | 114–6 | 51 |
| 19 | H | Me | Pr | Me | Et$_2$O | 170–2 | 31 |
| 20 | Me | Me | Me | Me | iPrOH/Et$_2$O | 158–160 | 78 |
| 21 | Me | Me | Et | Me | iPrOH/Et$_2$O | 144–6 | 59 |
| 22 | Me | Me | Pr | Me | iPrOH/Et$_2$O | ND | 60 |
| 26 | H | H | Pr | H | iPrOH/Et$_2$O | 209–11 | 20 |
| 27* | Me | Me | n-hexyl | Me | Et$_2$O | 95–7 | 13 |
| 28 | Me | Me | cyclohexyl | Me | Et$_2$O | 105–7 | 35 |
| 29** | H | Me | Me | H | iPrOH/Et$_2$O | 151–3 | 88 |
| 30** | H | Me | Et | H | iPrOH/Et$_2$O | 135–7 | 89 |
| 36 | H | Me | cyclohexyl | Me | Et$_2$O | 100–2 | 54 |

*mesylate salt
**substituted propargyl derivative, R6 in Scheme I is Me.

TABLE 3a

| # | stereo. | R3 | R4 | cryst/slurry solvent | mp (C.) | yield (%) |
|---|---------|----|----|---------------------|---------|-----------|
| 35 | rac | Me | Pr | EtOAc | 121–3 | 81 |
| 37 | R | Me | n-hexyl | " | 92–4 | 59 |
| 38 | S | Me | n-hexyl | " | 94–6 | 40 |
| 39 | S | Me | cyclohexyl | " | 118–20 | 63 |
| 40 | R | Me | cyclohexyl | " | 117–9 | 70 |

TABLE 4

Analytical Characteristics Relating To Compounds Of Table 2

| | NMR[1] | | | | | MS | elem. anal. |
|---|---|---|---|---|---|---|---|
| # | aryl | ethyl | R5 | R1, R2 | R3, R4 | IR | (MH+ (C, H, N) |
| 1 | 7.47, 7.27, 7.09 | 3.30, 3.02 | | | 3.13, 2.98 | | | |
| 2 | | | | | | 3095, 2975 1724, 1703 1461, 1401 | 237 | calc.: 5728, 7.70, 1027 found: 56.99, 7.88, 10.23 |
| 3 | 7.47, 7.27 7.10 | 3.36, 3.07 | | 2.73 | 3.16, 3.0 | 2941, 2775 2454, 1734 1384, 1237 | | calc.: 55.74, 7.35, 10.83 found: 55.47, 7.41, 10.85 |
| 4 | 7.46, 7.27 7.08 | 3.30 3.05 | | | 3.54, 3.39 3.13, 3.0 1.27, 1.19 | | | |
| 6 | 7.33, 7.12 7.02 | 3.35, 2.98 | | 2.54 | 3.24, 3.12 3.02, 2.90 1.60, 0.91 0.87 | | 251 | calc.: 58.63, 8.08, 9.77 found: 58.54, 8.04, 9.65 |

[1]D$_2$O, unless specified otherwise

TABLE 5
Analytical Characteristics of Compounds of Table 3
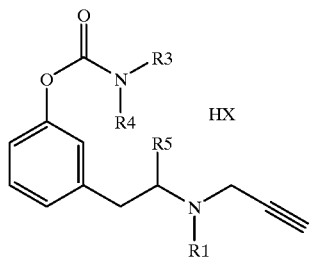
| # | aryl | ethyl | R5 | R1 | proparg. | R3, R4 | IR | MS (MH+) | elem. anal. (C, H, N) |
|---|------|-------|----|----|----------|--------|----|---------|----|
| 11 | 7.48, 7.27 7.11 | 3.50, 3.11 | | | 3.96, 3.02 | 3.16, 3.01 | 3230, 2934 2782, 1713 1393, 1275 | 247 | calc.: 59.46, 6.77, 9.91 found: 59.26, 6.84, 9.90 |
| 12 | 7.43, 7.24 7.06 | 3.55 3.11 | | 2.96 | 4.08, 3.11 | 3.10, 2.98 | 3197, 2935 2616, 1730 1388, 1242 | 261 | .: 60.70, 7.13, 9.44 found: 60.50, 7.04, 9.32 |
| 13 | 7.43, 7.22 7.07 | 3.43 3.05 | | | 3.90, 2.96 | 3.50, 3.34 3.09, 2.95 1.23, 1.15 | 3228, 2934 2781, 1707 1395, 1248 | 261 | calc.: 60.70, 7.08, 9.44 found: 60.51, 7.13, 9.39 |
| 14 | 7.45, 7.25 7.08 | 3.47 3.07 | | | 3.82, 2.98 | 3.47, 3.31 3.11, 2.96 1.67, 0.98 0.95 | | 275 | calc.: 61.83, 7.40, 9.01 found: 61.70, 7.29, 9.24 |
| 15 | 7.45, 7.27 7.10 | 3.57 3.15 | | 3.0 | 4.10, 3.15 | 3.55, 3.37 3.12, 2.97 1.25, 1.17 | 3299, 2905 1725, 1485 1396 | 275 | calc.: 61.83, 7.46, 9.01 found: 61.05, 7.40, 8.88 |
| 16 | 7.57, 7.35 7.24 | 3.50 3.36 3.10 | 1.47 | | 4.21, 3.45 | 3.18, 3.31 | 3262, 2935 1699, 1394 1241, 1171 | 261 | calc.: 60.70, 7.08, 9.44 found: 60.57, 7.10, 9.28 |
| 17 | 7.45, 7.23 7.10, 7.08 | 3.75 3.52 3.38 | 1.30 | | 3.96, 2.97 | 3.12, 3.11 2.97, 2.95 1.25, 1.17 | 3420, 1709 1402, 1242 1171 | 275 | calc.: 61.83, 7.40, 9.01 found: 61.58, 7.36, 8.98 |
| 18 | 7.46, 7.26, 7.08 | 3.56 3.14 | | 3.0 | 4.10, 3.11 | 3.46, 3.32 3.11, 2.98 1.66, 0.96 0.92 | 3446, 3203 2940, 2622 1722, 1468 1402, 1232 | 289 | calc.: 62.85, 7.76, 8.63 found: 62.67, 7.69, 8.59 |
| 19 | 7.47, 7.26 7.10 | 3.80 3.48 3.33 | 1.33 | | 4.0, 3.02 | 3.15, 3.14 3.0, 2.95 1.7, 0.97 0.92 | 3448, 2937 1733, 1403 1232, 1165 | 289 | calc.: 62.86, 7.70, 8.63 found: 63.0, 7.87, 8.62 |
| 20 | 7.50, 7.29 7.15 | 4.02 3.25 2.97 | 1.33 | 2.99 | 4.15, 3.18 | 3.18, 3.02 | 3413, 3182 2928, 2491 2120, 1724 1392, 1172 | 275 | calc.: 61.83, 7.46, 9.02 found: 61.58, 7.48, 8.85 |
| 21 | 7.48, 7.29 7.14 | 3.98 3.23 2.97 | 1.32 | 2.95 | 4.12, 3.15 | 3.55, 3.40 3.16, 3.02 1.29, 1.22 | | 289 | calc.: 62.85, 7.76, 8.68 found: 62.84, 7.93, 8.83 |
| 22 | 7.49, 7.28 7.13 | 4.01 3.23 2.97 | 1.32 | 2.96 | 4.12, 3.18 | 3.50, 3.35 3.16, 3.02 1.70, 0.99 0.93 | | 303 | calc.: 63.81, 7.97, 8.27 found: 62.23, 8.01, 7.85 |
| 26 | 7.49, 7.28 7.13 | 3.50 3.11 | | | 3.96, 3.02 | 3.21, 1.61 0.98 | | 261 | |
| 27 | 7.42, 7.26 7.02 | 3.92 3.43 3.33 | 1.31 | 2.95 | 4.11, 3.16 | 3.21, 3.06 2.95, 1.62 1.28, 0.88 | | | calc.: 56.48, 8.57, 6.27 found: 55.85, 7.94, 5.71 |
| 28 | 7.50, 7.29 7.12 | 4.05 3.27 3.23 | 1.33 | 3.0 | 4.15, 3.17 | 3.0, 2.0–1.0 | | | calc.: 66.57, 8.19, 7.39 found: 66.10, 8.28, 7.10 |
| 29* | 7.47, 7.27 7.10 | 3.57 3.43 3.09 | | | 4.25, 3.10 1.58 | 3.15, 3.0 | | 261 | calc.: 60.70, 7.13, 9.44 found: 60.76, 7.31, 9.13 |
| 30* | 7.49, 7.29 7.12 | 3.50 3.43 3.14 | | | 4.27, 3.13 1.60 | 3.58, 3.43 3.12, 3.0 1.27, 1.21 | | 275 | calc.: 61.83, 7.46, 9.02 found: 61.62, 7.42, 8.98 |
| 35 | 7.49, 7.30 7.13 | 4.05 3.50 3.35 | 1.33 | 3.0 | 4.15, 3.15 | 3.16, 3.0, 1.69, 0.96 | | 303 | calc.: 58.22, 7.82, 6.79 found: 57.92, 7.83, 6.79 |

TABLE 5-continued

Analytical Characteristics of Compounds of Table 3

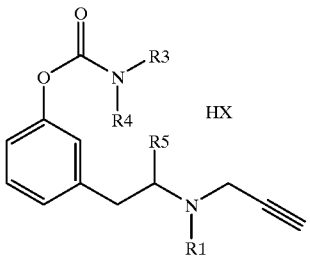

| # | aryl | ethyl | R5 | R1 | proparg. | R3, R4 | IR | MS (MH+) | elem. anal. (C, H, N) |
|---|------|-------|-----|------|----------|--------|-----|----------|------------------------|
| 36 | 7.47, 7.27, 7.11 | 4.10 3.88 3.16 2.98 | 1.34 | | 4.00, 3.03 | 3.80, 3.00, 1.85, 1.65, 1.35, 1.18 | | | calc.: 66.02, 7.70, 7.70 found: 65.81, 7.42, 7.98 |
| 38 | 7.47, 7.28, 7.11 | 4.01 3.52 3.38 | 1.32 | 2.98 | 4.14, 3.13 | 3.23, 3.17, 2.99, 1.68, 1.36, 0.90 | | 345 | calc.: 60.17, 8.45, 6.10 found: 60.17, 8.41, 6.20 |
| 39 | 7.49, 7.28, 7.12 | 4.05 3.25 2.98 | 1.32 | 2.98 | 4.15, 3.17 | 3.90, 2.97, 1.85, 1.65 1.35, 1.16 | | | calc.: 61.03, 8.02, 6.19 found: 60.78, 8.13, 5.93 |

*substituted propargyl derivative, R6 in Scheme I is Me.
[2]$D_2O$, unless specified otherwise

BIOLOGICAL EXAMPLES

Example 1

Acetylcholinesterase Inhibition in Mice 1.1. In Vitro Measurement of Acetylcholinesterase (AChE) Inhibition Human erythrocyte acetylcholinesterase (type XIII, Sigma Israel), was prepared in a stock solution of 1 U/ml, containing Triton (1%) and bovine serum albumin (0.05%) in phosphate buffer (pH 8). The enzyme (0.05U) was incubated with 3–5 different concentrations of test compound (in triplicate) for periods of from 15 to 60 minutes at 37° C. The substrate acetylthiocholine (0.975 M) and 5,5'-dithiobis-(2-nitrobenzoic acid) (DTNB, 0.01 M) were then added and the rate of hydrolysis of the substrate which yields a yellow product monitored spectrophotomerically at 412 nM (Eliman, et al., *Biochem Pharmacol.* (1961) 7: 88–95). The percentage inhibition of AChE by each concentration of drug is calculated by comparison with that of enzyme in the absence of drug. The concentration of each drug that inhibits ACHE by 50% ($IC_{50}$) at the time of peak activity was calculated and is given in Table 6 below.

1.2 Ex Vivo Measurement of Acetylcholinesterase (AChE) Inhibition

Test drugs or saline were administered sub-cutaneously to male mice (Sabra strain, 28–35 g). At least 4–5 mice were used per dose and a minimum of 3 doses per drug were tested. The mice were sacrificed 15, 30, 60, 70, 90, 120 or 180 minutes after drug administration, the brains rapidly removed (minus cerebellum), weighed and homogenized in 0.1M phosphate buffer pH 8.0, containing Triton (1 mg/100 g tissue) and centrifuged to remove cell debris. Aliquots (25 $\mu$l) of the supernatant were then incubated with acetylthiocholine and DTNB. AChE activity measured as described above. The % inhibition of whole brain ACHE by each dose of drug was calculated by comparison with enzyme activity from 3 saline treated control mice run at the same time. The dose of each drug that inhibits AChE by 50% at the peak of activity ($ED_{50}$) was calculated and is given in Table 6.

1.3 Acute Toxicity in Mice

Drugs were administered sub-cutaneously in at least 3 doses, to a minimum of 10 mice per dose. The dose that was lethal to 50% of the mice (LD50) within 6 hours after administration was calculated for each drug and is given in Table 6. Therapeutic Ratio was calculated as $LD_{50}$ divided by $ED_{50}$(acetylcholine esterase ex vivo).

Example 2

2.1 Inhibition of MAO Activity in Vitro

The MAO enzyme source was a homogenate of rat brain in 0.3 M sucrose, which was centrifuged at 600 g for 15 minutes. The supernatant was diluted appropriately in 0.05 M phosphate buffer, and pre-incubated with serial dilutions of test compounds for 20 minutes at 37° C. $^{14}$C-Labeled substrates (2-phenylethylamine, hereinafter PEA; 5-hydroxytryptamine, hereinafter 5-HT) were then added, and the incubation continued for a further 20 minutes (PEA), or 30–45 minutes (5-HT). Substrate concentrations used were 50$\mu$M (PEA) and 1 mM (5-HT). In the case of PEA, enzyme concentration was chosen so that not more than 10% of the substrate was metabolized during the course of the reaction. The deaminated products were extracted into toluene-ethyl acetate (1:1, v/v) containing 0.6% (w/v) 2,5-diphenyloxazole prior to determination by liquid scintillation counting. Radioactivity in the eluate indicates the production of neutral and acidic metabolites formed as a result of MAO activity. Activity of MAO in the sample was expressed as a percentage of control activity in the absence of inhibitors after subtraction of appropriate blank values. The activity determined using PEA as substrate is referred to as MAO-B, and that determined using 5-HT as MAO-A.

Concentrations of inhibitor producing 50% inhibition of substrate metabolism (ICso) were calculated from the inhibition curves, and are shown in Table 6.

2.2 Inhibition of MAO Activity Ex Vivo

Male Sabra mice, weighing 45–50 g were injected with test compound solutions (prepared in 0.9% saline). Each dose was administered to two or three mice. The mice were sacrificed two hours after drug administration or at a time corresponding to the peak AChE inhibition time (see Table 6). The brain and liver were rapidly dissected and stored in appropriate vials on ice. The tissues were weighed, diluted to $\frac{1}{20}$ in sucrose 0.3 M and stored at $-20°$ C. before performance of the MAO assay described above. The results given in Table 6 relate to measurements made on brain tissue only.

2.3 Inhibition of MAO Activity Following Sub-Acute Administration to Rats

Experiments were done with Spague Dawley male rats. Procedures were repeated as described in Examples 2.1 and 2.2, but drug administration was continued daily for 14 days. At the end of this period animals were sacrificed and MAO levels determined in the brain, liver and intestines. Compound 17 was administered sub-cutaneously or per os at a dose of 20 mg/kg. The results are shown in Table 6a.

TABLE 6

| | AChE Inhibition | | Time | | MAO-B Inhibition | | MAO-B Inhibition | | Acute Toxicity | |
|---|---|---|---|---|---|---|---|---|---|---|
| | | Ex vivo | | to return to | | | | | | |
| | In vitro IC50 μM | ED50 μmoles/kg (AC) | to peak activity t (min) | 50% of peak t (min) | In vitro IC50 μM | Ex vivo ED50 μmoles/kg | In vitro IC50 μM | Ex vivo ED50 μmoles/kg | LD50 μmoles/kg | Therapeutic Ratio (LD/AC) |
| 11 | 0.82 | 3.2 | 15 | 70 | 25 | >>30 | 2.5 | 40 | 44.2 | 13.8 |
| 12 | 0.88 | 2.8 | 15–30 | 120 | 2.5 | 21 | 0.38 | 4 | 46 | 11.5 |
| 13 | 30.0 | 53.8 | 30–90 | 120 | 8.3 | 50 | 3.3 | 75 | 458 | 8.5 |
| 14 | 12.5 | 100 | 30 | | 0.3 | 0.6 | 1.8 | 4.5 | | |
| 15 | 67.2 | 145 | 30 | | 1 | 35 | 1 | 35 | 1250 | 8.6 |
| 16 | 0.37 | 2.3 | 15 | 70 | 6 | >20 | 7 | >20 | 42 | 18.3 |
| 17 | 36.0 | 64 | 30–60 | 120 | 2 | 40 | 12 | >40 | 600 | 9.4 |
| 19 | 20.0 | 170 | 30–60 | | 0.17 | 1.5 | 14.6 | >70 | 1300 | 7.6 |
| 1 | 0.31 | NT | | | >1000 | | 100 | | | |
| 4 | 48.4 | NT | | | >1000 | | 200 | | | |
| 2 | 8.2 | NT | | | >1000 | | 500 | | | |
| 3 | 0.31 | 39.2 | 10 | 30 | >1000 | | 50 | | 57.7 | 1.5 |
| 5 | 20.8 | NT | | | >1000 | >>160 | 25 | >>160 | | |
| 10 | 0.2 | 2.0 | 15–30 | | >1000 | | 51 | | 16 | 8 |
| 31 | | | | | 500 | | 500 | | | |
| 32 | | | | | 100 | 200 | 67 | >>200 | | |
| 33 | | | | | 5 | >10 | 1.8 | >10 | | |
| 20 | 1.7 | 15 | | | 0.4 | 7 | 0.12 | 6 | 170 | 11.3 |
| 21 | 230 | | | | 0.2 | | 0.12 | | | |
| 27 | 3.1 | >50 | | | 1.5 | 3.4 | 20 | >430 | >1000 | |
| 29 | 0.15 | 2.5 | | | | >>12.5 | | >>12.5 | | |
| 30 | 14 | 45 | | | | >>270 | | >>270 | | |
| 28 | 11.5 | 21 | 60 | | 0.24 | 1.75 | 1.7 | 109 | 2000 | >47 |
| 34 | | | | | >1000 | | 500 | | | |
| 35 | 50 | >200 | | | | | | | | |
| 36 | 3.4 | >50 | | | | | | | | |
| 38 | 3.1 | >50 | | | | | | | | |

TABLE 6a

Effect of compound 17 on MAO activity following sub-acutechronic treatment

| Organ | Administration | % MAO-A inhibition | % MAO-B inhibition |
|---|---|---|---|
| Brain | sc | 76 | 87 |
| | po | 59 | 72 |
| Intestine | sc | 10 | 33 |
| | po | 25 | 40 |

TABLE 6a-continued

Effect of compound 17 on MAO activity following sub-acutechronic treatment

| Organ | Administration | % MAO-A inhibition | % MAO-B inhibition |
|---|---|---|---|
| Liver | sc | 33 | 51 |
| | po | 59 | 74 |

Example 3

Effect of Drug Treatment Following Closed Head Injury(C) in Mice

The procedure for closed head injury followed was as described for rats in Shohami et al. (J. Neurotrauma (1993) 10(2) 109–119) with changes as described.

Animals: Male Sabra mice (Hebrew University strain) weighing 34–40 g were used. They were housed in groups of 10 per cage, in a 12 hr:12 hr light:dark cycle. Food and water were provided ad libitium.

Trauma was induced under ether anesthesia. A longitudinal incision was performed in the skin covering the skull and the skin retracted to expose the skull. The head was fixed manually at the lower plane of the impact apparatus. A weight of 333 g was delivered by an electric device from a height of 3 cm to the left hemisphere, 1–2 mm lateral to the midline in the midcoronal plane. Test compounds were injected sub-cutaneously at a dosage corresponding to the $ED_{50}$ for acetylcholinesterase inhibition, once 15 min. after CHI.

3.1 Assessment of Motor Function.

Motor function and reflexes were evaluated in the injured-mice at different times after. closed head injury (CHI) using a neurological severity score (NSS) as shown in Table 7 below, which is modified from that described for rats (Shohami et al. supra.). One point was awarded for the lack of a tested reflex or for the inability to perform the tasks outline in the Table. The maximal score that can be reached at 1 hour post-CHI is 25 points and 21 at later times. The difference in NSS at 1 hr and at any other time reflects the recovery, and is referred to as NSS. An NSS score of 15–19 at 1 hr denotes severe injury, 11–14 moderate injury and less than 10 mild injury. The NSS recorded after treatment with test compound or control is shown in Table 8.

TABLE 7

Neurological Severity Score for Mice After Closed Head Injury

| Parameter | Points at 1 hr | Points at any other time |
|---|---|---|
| Inability to exit from a circle (30 cm diameter) when left in its center | | |
| for 30 min | 1 | |
| for 60 min | 1 | |
| for >60 min | 1 | 1 |
| Loss of righting reflex | | |
| for 10 second | 1 | |
| for 20 seconds | 1 | |
| for >30 seconds | 1 | 1 |
| Hemiplegia - inability of mouse to resist forced changes in position | 1 | 1 |
| Flexion of hind limb when lifted by tail | 1 | 1 |
| Inability to walk straight when placed on the floor | 1 | 1 |
| Reflexes | | |
| Pinna reflex | 1 | 1 |
| Corneal reflex | 1 | 1 |
| Startle reflex | 1 | 1 |
| Clinical grade | | |
| Loss of seeking behavior | 1 | 1 |
| Prostration | 1 | 1 |
| Loss of reflexes | | |
| Left forelimb | 1 | 1 |
| Right forelimb | 1 | 1 |
| Left hindlimb | 1 | 1 |
| Right hindlimb | 1 | 1 |
| Functional test | | |
| Failure in beam balancing task (0.5 cm wide) | | |
| for 20 seconds | 1 | 1 |
| for 40 seconds | 1 | 1 |
| for >60 seconds | 1 | 1 |
| Failure in round stick balancing task (0.5 cm in diameter | | |
| for 10 seconds | 1 | 1 |
| Failure in beam walking task | | |
| 3 cm wide | 1 | 1 |
| 2 cm wide | 1 | 1 |
| 1 cm wide | 1 | 1 |
| Maximum Points | 25 | 21 |

Results
Assessment of Motor Function.

TABLE 8

Change in Neurological Severity Score after Closed Head Injury in Mice

| Drug/dose | N | ΔNSS, 24 hr post-CHI | ΔNSS, 7 days post-CHI | ΔNSS, 14 days post-CHI |
|---|---|---|---|---|
| Saline, 1 ml/kg | 51 | 4.75 ± 0.17 | 5.83 ± 0.36 | 5.96 ± 0.4 |
| 17 | 12 | 5.58 ± 0.38* | 6.92 ± 0.36* | 7.83 ± 0.53* |

*significantly different from saline control ($p < 0.05$)

3.2 Assessment of Reference Memory

Morris Water Maze Test: the water maze consists of a circular aluminium pool, 1 m in diameter and 60 cm in depth, filled with water to a depth of 17.5 cm. The hidden goal platform is a glass vessel (15 cm diameter×16.5 cm height) placed upside down at a fixed location in the pool, 1 cm below the surface of the water. The water temperature is maintained at 24° C. and the pool is always placed in the same position in the room to provide the same extra-maze cues. Prior to CHI (as described in Example 3 above), mice were given 3 trials per day for 5 consecutive days to establish a baseline performance—measured as the latency to find the platform from the same start location. Commencing 24 hr after CHI, mice were retested daily for 2 weeks in 3 trials per day.

BRIEF DESCRIPTION OF THE DRAWINGS

FIG. 1 shows the reduction in latency for mice treated with compound 17 compared to saline treated controls after CHI. It appears that immediately post-CHI mice forget the location of the goal. Memory is enhanced following treatment with test compounds, as compared to saline treated mice. In FIG. 1 the arrow shows the time of CHI.

Example 5

Effect on Mice having Experienced a Hypobaric Hypoxic Episode

The hypobaric hypoxic model is a well accepted model for assessing the activity of compounds believed to possess neuroprotective activity. The model is based on that described in Nakanishi, M. et al. *Life Sci.* (1973) 13: 467; Oshiro, et al., *J. Med. Chem.* (1991) 34: 2004–2013; and U.S. Pat. No. 4,788,130.

A 12 liter desiccator (desiccator A) and a 2.5 liter desiccator (desiccator B) were separately connected to a vacuum pump. Desiccator B was. disconnected and allowed to equilibrate with room air whilst desiccator A was evacuated to a pressure of 100 mmHg. Four male ICR albino mice (22–28 g) were placed in desiccator B. Desiccator B was then closed to room air and connected to desiccator A. The pressure inside desiccator B was monitored using a mercury manometer and at the point were the pressure in desiccator B reached 200 mmHg (usually within 14 seconds), the two desiccators were disconnected from the vacuum pump and the pump switched off. The survival time from the moment of induction of hypoxia to the time of cessation of respiration was recorded for each mouse for a maximum of 15 minutes after which time room air was reintroduced to desiccator B. Survivors were monitored for signs of lethargy or vitality.

Effect of drug treatment was assessed as the percent of the survival time of the drug treated group with respect to the saline injected or vehicle injected control group. Control groups were run twice, before and after each experimental group and consisted of 8 mice in groups of 4 mice to ensure a constant residual volume of oxygen in all tests. The effect of each dose of test drug was determined in duplicate i.e. two groups of 4 mice. The range of survival times of control mice was from 108–180 seconds.

Positive reference drugs were sodium pentobarbital at a dose of 40 mg/kg, and diazepam 10 mg/kg given 0.5 h prior to hypoxia, physostigmine 0.2 and 0.4 mg/kg and neostigmine 0.2 mg/kg given sc 30 min before hypoxia. Methyl atropine 1 mg/kg was given sc. 10 min. before physostigmine.

Test drugs were dissolved in 0.9% saline, and injected sc. in the nip of the neck at a dose in accordance with body weight, 60–90 min. before hypoxia. The volume of injection was 0.2–0.3 mL per mouse (10 mL/kg). The initial dose was about one third of the reported $LD_{50}$ for acetylcholine esterase inhibition. If no protection could be obtained, the dose was further increased to the nearest non-toxic dose. In case of protection, the dose was further reduced in an attempt to locate the "protective" dose range.

Percent survival times as compared to saline treated control is shown in Table 9.

TABLE 9

Survival Time of Mice Having Experienced a Hypobaric Episode

| Compound | Dose mg/kg | Time of dose (min before hypoxia) | Protection (% of control) | p |
|---|---|---|---|---|
| Control (saline) | | | 100 | |
| Nembutal | 40 | 30 | 253 ± 200 | <0.005 |
| Diazepam | 10 | 30 | 316 ± 78 | <0.003 |
| Neostigmine | 0.2 | 30 | 141 ± 32 | <0.01 |
| Physostigmine | 0.2 | 30 | 453 ± 222 | <0.001 |
| | 0.4 | 30 | 552 ± 210 | <0.001 |
| Physostigmine and Atropine methyl nitrate | 0.4 | 30 | 296 ± 193 | <0.05 |
| | 1.0 | 40 | | |
| 11 | 6.2 | 60 | 331 ± 168 | |
| | 4.1 | 60 | 416 ± 211 | |
| | 4.1 | 30 | 501 ± 201 | |
| | 2 | 60 | 128 ± 40 | |
| | 2 | 30 | 302 ± 212 | |
| 12 | 7 | 60 | 217 ± 120 | <0.02 |
| | 4.5 | 60 | 97 ± 36 | NS |
| 17 | 94 | 60 | 281 ± 158 | <0.001 |
| | 62 | 60 | 419 ± 122 | <0.001 |
| | 31 | 60 | 149 ± 44 | <0.05 |
| 16 | 15 | 60 | toxic | |
| | 6.2 | 60 | 324 ± 155 | <0.001 |
| | 4.1 | 60 | 335 ± 202 | <0.01 |
| 19 | 75 | 60 | 773 ± 228 | p < 0.001 |
| | 50 | 60 | 309 ± 253 | p < 0.05 |
| | 25 | 60 | 169 ± 50 | p < 0.01 |

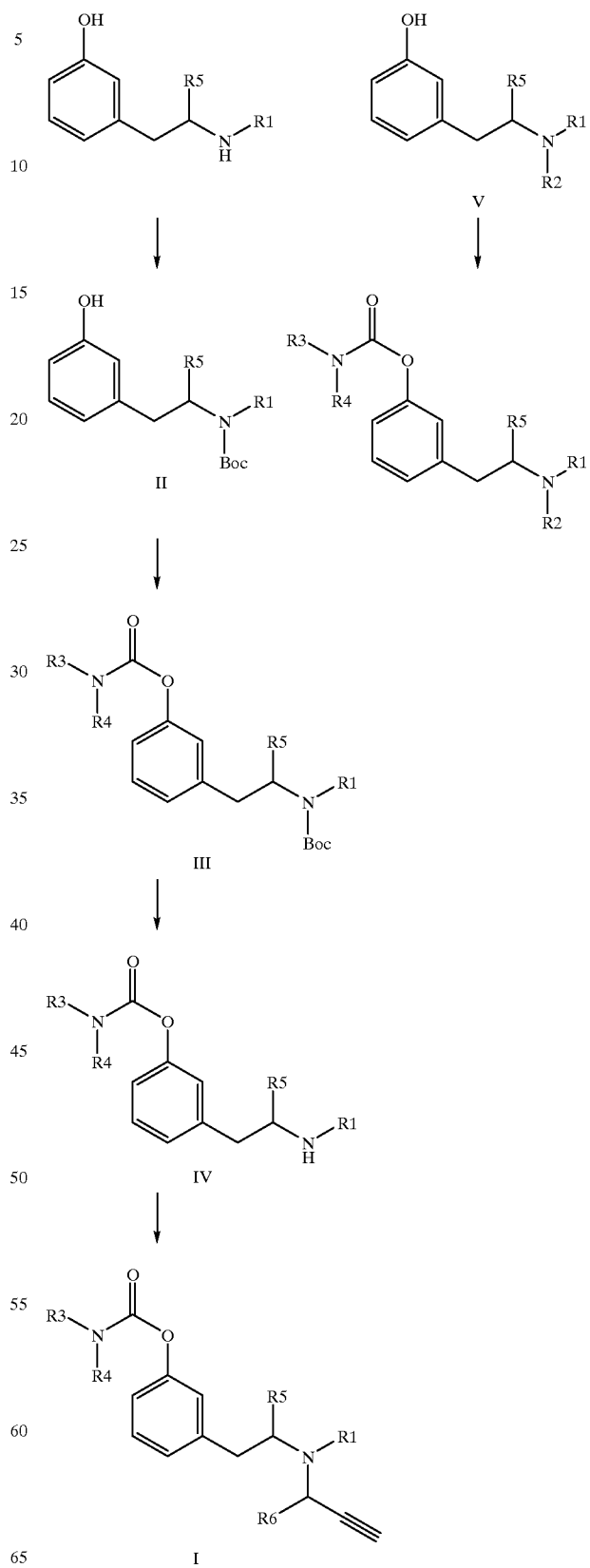

SCHEME I

SCHEME II

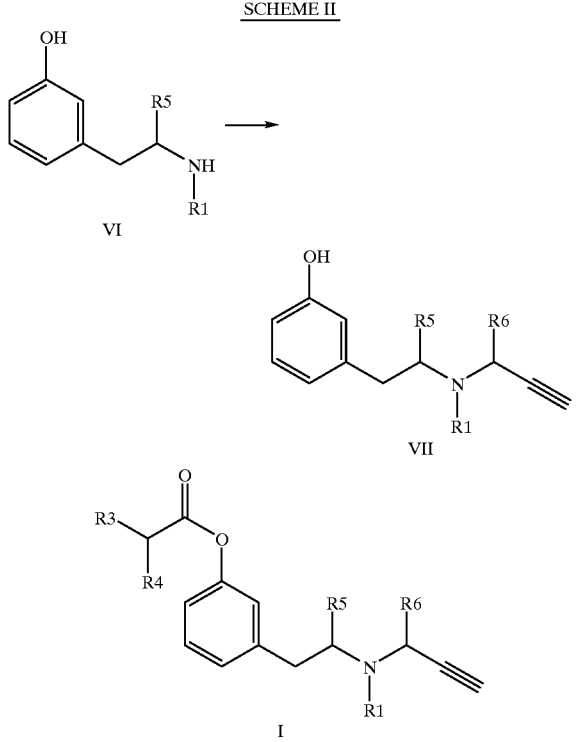

What is claimed is:
1. A compound having the formula:

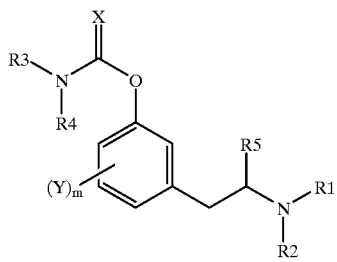

wherein
m is from 0–4;
X is O or S;
Y is halogeno;
$R_1$ is hydrogen or $C_{1-4}$ alkyl;
$R_2$ is hydrogen, $C_{1-4}$ alkyl or optionally substituted propargyl; and
$R_3$ and $R_4$ are each independently hydrogen, $C_{1-8}$ alkyl, $C_{6-12}$ aryl, $C_{6-12}$ cycloalkyl or $C_{6-12}$ aralkyl, $R_5$ is hydrogen or $C_{1-4}$ alkyl; and pharmaceutically acceptable salts thereof, provided that when X is O, $R_2$ is optionally substituted propargyl.

2. A compound according to claim 1 wherein X is O.
3. A compound according to claim 1 wherein X is S.
4. A compound according to claim 1, wherein the compound is selected from the group consisting of: (rac)-3-(N-methyl,N-propyl-carbamyloxy)-α-methyl-N'-propargyl phenethylamine HCl; (rac)-3-(N,N-dimethyl-carbamyloxy)-α-methyl-N'-methyl,N'-propargyl phenethylamine HCl; (rac)-3-(N-methyl,N-hexyl-carbamyloxy)-α-methyl-N'-methyl, N'-propargyl phenethylamine mesylate; (rac)-3-(N-methyl,N-cyclohexyl-carbamyloxy)-α-methyl-N'-methyl, N'-methyl,N'-propargyl phenethylamine HCl; and (S)-3-(N-methyl, N-hexyl-carbamyloxy)-α-methyl-N'-methyl,N'-propargyl phenethylamine ethanesulfonate.

5. A compound according to claim 1, wherein at least one of $R_3$ and $R_4$ is methyl and the other is hydrogen, methyl, ethyl, propyl, hexyl or cyclohexyl.
6. A compound according to claim 2, wherein at least one of $R_3$ and $R_4$ is methyl and the other is hydrogen, methyl, ethyl, propyl, hexyl or cyclohexyl.
7. A compound according to claim 1, wherein said compound is an optically active enantiomer.
8. A compound according to claim 2, wherein said compound is an optically active enantiomer.
9. A compound according to claim 3, wherein said compound is an optically active enantiomer.
10. A compound according to claim 4, wherein said compound is an optically active enantiomer.
11. A compound according to claim 1, wherein $R_2$ is an optionally substituted propargyl.
12. A compound according to claim 2, wherein $R_2$ is an optionally substituted propargyl.
13. A compound according to claim 3, wherein $R_2$ is an optionally substituted propargyl.
14. A compound according to claim 4, wherein $R_2$ is an optionally substituted propargyl.
15. A method of treating neurotrauma, ADD, ADHD, Tourette's Syndrome, memory disorder or depression which comprises administering an effective amount of the compound of claim 1.
16. The method of claim 15, wherein neurotrauma includes central nervous system damage and peripheral nervous system damage.
17. A pharmaceutical composition comprising a therapeutically effective amount of the compound of claim 1 and a pharmaceutically acceptable carrier.
18. A pharmaceutical composition comprising a therapeutically effective amount of the compound of claim 2 and a pharmaceutically acceptable carrier.
19. A pharmaceutical composition comprising a therapeutically effective amount of the compound of claim 3 and a pharmaceutically acceptable carrier.
20. A pharmaceutical composition comprising a therapeutically effective amount of the compound of claim 4 and a pharmaceutically acceptable carrier.
21. A method of treating a subject suffering from Alzheimer's disease or dementias which comprises administering to the subject an amount of the compound of claim 1 effective to treat Alzheimer's disease or dementias.
22. A method of treating a subject suffering from Alzheimer's disease or dementias which comprises administering to the subject an amount of the compound of claim 2 effective to treat Alzheimer's disease or dementias.
23. A method of treating a subject suffering from Alzheimer's disease or dementias which comprises administering to the subject an amount of the compound of claim 3 effective to treat Alzheimer's disease or dementias.
24. A method of treating a subject suffering from Alzheimer's disease or dementias which comprises administering to the subject an amount of the compound of claim 4 effective to treat Alzheimer's disease or dementias.
25. The method of claim 24, wherein demencias include static dementia, Alzheimer's-type dementia, senile dementia, presenile dementia, progressive dementia, vascular dementia or Lewy body dementia.
26. The method of claim 22, wherein dementias include static dementia, Alzheimer's-type dementia, senile dementia, presenile dementia, progressive dementia, vascular dementia or Lewy body dementia.

27. The method of claim 23, wherein dementias include static dementia, Alzheimer's-type dementia, senile dementia, presenile dementia, progressive dementia, vascular dementia or Lewy body dementia.

28. The method of claim 24, wherein dementias include static dementia, Alzheimer's-type dementia, senile dementia, presenile dementia, progressive dementia, vascular dementia or Lewy body dementia.

* * * * *